United States Patent [19]

Krüger

[11] Patent Number: 4,612,927

[45] Date of Patent: Sep. 23, 1986

[54] INSTRUMENT FOR KEEPING CLEAR THE UPPER RESPIRATORY PASSAGES

[76] Inventor: Christian Krüger, Curtiusstrasse 4, 2400 Lübeck, Fed. Rep. of Germany

[21] Appl. No.: 689,662

[22] Filed: Jan. 8, 1985

[30] Foreign Application Priority Data

Jan. 12, 1984 [DE] Fed. Rep. of Germany ....... 3400872

[51] Int. Cl.⁴ ............................................ A61M 16/00
[52] U.S. Cl. ................................................ 128/200.26
[58] Field of Search ...................... 128/200.26, 207.15, 128/207.14, 3, 4, 10, 12, 15, 16; 604/280

[56] References Cited

U.S. PATENT DOCUMENTS

| | | | |
|---|---|---|---|
| 3,154,069 | 10/1964 | Ring | 128/15 |
| 4,256,099 | 3/1981 | Dryden | 128/200.26 |
| 4,338,930 | 7/1982 | Williams | 128/200.26 |
| 4,449,526 | 5/1984 | Elam | 128/207.14 |
| 4,454,887 | 6/1984 | Kruger | 128/207.14 |
| 4,502,482 | 3/1985 | DeLuccia et al. | 128/207.15 |

Primary Examiner—Henry J. Recla
Attorney, Agent, or Firm—Balogh, Osann, Kramer, Dvorak, Genova & Traub

[57] ABSTRACT

The invention relates to an instrument for keeping clear the upper respiratory passages and for performing intubations, in which a tube which is to be inserted may have its distal extremity moved as far as into the windpipe via a passage acting as a guide. The passage is constructed as a channel extending within the instrument shaft, whereas the distal instrument extremity comprises a head before which terminates the channel and which is intended to be placed in contact against the larynx upon inserting the instrument. The instrument head acting as a stop will thus limit the maximum depth of insertion.

1 Claim, 15 Drawing Figures

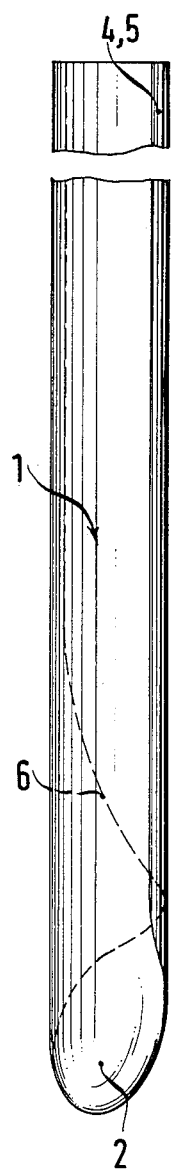
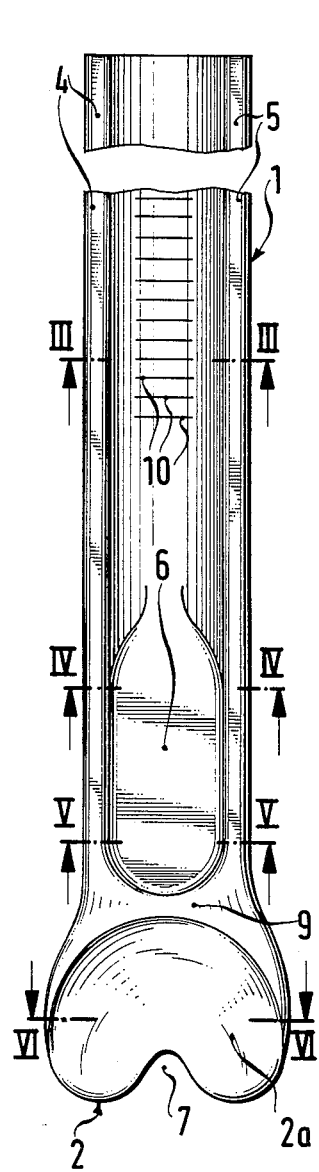
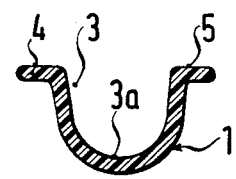
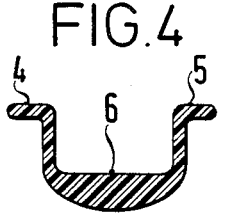
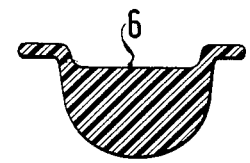
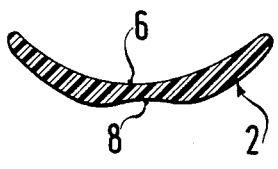

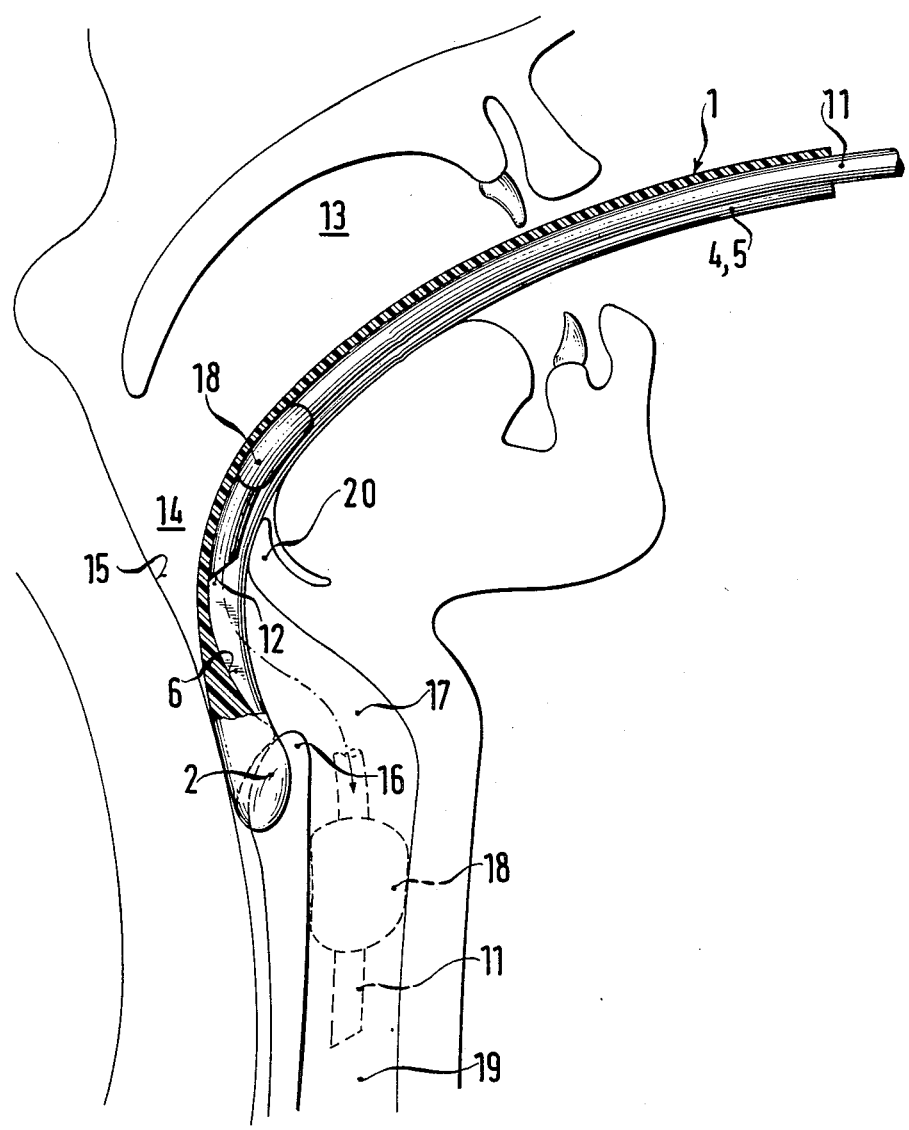

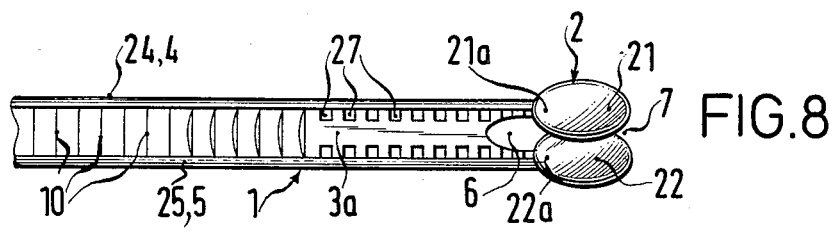
FIG.8
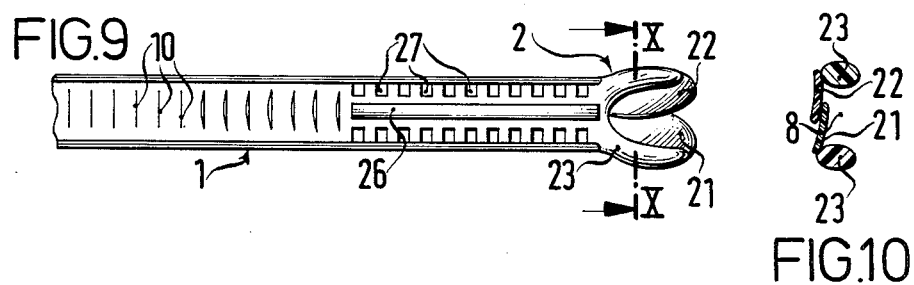
FIG.9
FIG.10
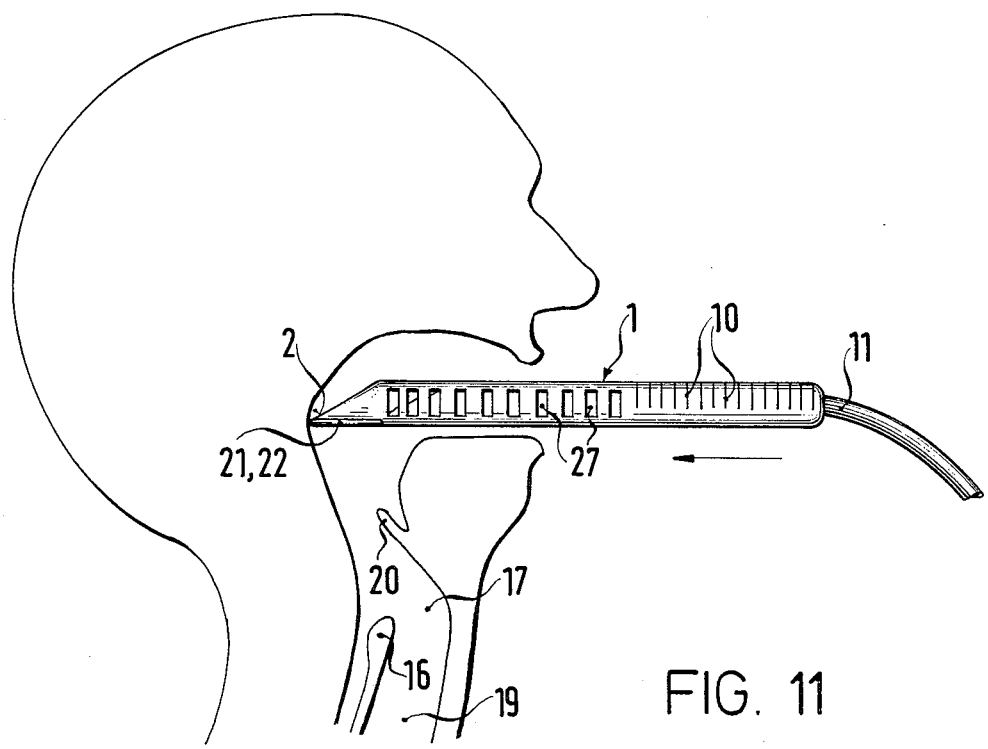
FIG. 11

INSTRUMENT FOR KEEPING CLEAR THE UPPER RESPIRATORY PASSAGES

BACKGROUND OF THE INVENTION

1. Field of the Invention

The invention relates to an instrument for keeping clear the upper respiratory passages, and for performing intubations, in which a tube which is to be inserted has its distal extremity moved as far as into the trachea via a passage acting as a guide.

2. Description of the Prior Art

An orotracheal intubation is applied, amongst other applications, in cases of acute respiratory distress or air starvation, to establish an unobstructed respiratory passage through the tube inserted into the windpipe. To this end, the tube had primarily been inserted "blind" or "by feel" during initial application of this method. Only the development of different laryngoscopes led to the now customary method of intubation under observation.

An intubation by means of a laryngoscope may normally be performed without complications as well as comparatively quickly, by a competent physician. It is disadvantageous however that the patient has to be positioned in a special manner and that the physician must have freedom of movement at the patient's head. The preparations required for this purpose imply a commensurate expenditure of time. Inexperienced physicians moreover not infrequently encounter difficulties in inserting the instrument correctly and in making an "optical adjustment" of the larynx, so that injuries may for example be caused to the front incisors. Furthermore, the comparatively expensive laryngoscopes are not always available either. Finally, servicing and sterilising operations after use are finally rendered necessary on a regular basis by these instruments.

For this reason, attempts were repeatedly made in the course of time to discover appropriate methods of inserting the tube "by feel", although this operation has to be performed without observation. It was thus already proposed to insert the tube by means of a mandrel. This method failed to gain acceptance, however. Until now, only the transnasal intubation held its own as a tactile method in case of special indications, which however also presupposes that the physician has some experience of this technique and is unreliable in particular inasmuch as the tube cannot always be inserted into the windpipe through the pharyngeal cavity with identical precision and without the risk of injury.

SUMMARY OF THE INVENTION

One object of the invention consists in devising an intubation instrument which may be utilised safely, rapidly and without risk by less experienced physicians and even laymen after appropriate training. The production of the instrument should be inexpensive moreover, so that it is also appropriate as an item for once-only use and that it may enjoy commensurately wide distribution, for emergency intubation amongst other applications.

To resolve this problem, the instrument defined in the foregoing is so constructed in accordance with the invention that the passage is constructed as a channel extending within the instrument shaft and that the distal instrument extremity comprises a head before which terminates the said channel and which is to be placed in contact with the larynx when inserting the instrument and acts as a stop to limit the maximum depth of insertion.

In the breathing position, the larynx is in direct contact with the pharyngeal surface and travels forwardly and upwardly along an arcuate line during the swallowing action, whilst moving away from the pharyngeal surface. Conversely, the larynx is pressed more closely against the pharynx by an induced and downwardly directed movement. In accordance with these anatomical conditions, the wholly inserted instrument will have its distal head bearing against the larynx, and partially enflank and downwardly depress the same. The instrument head is concomitantly clamped between the larynx and the pharynx at the same time. This position should be maintained in a fixed relationship with respect to the other dimensions of the larynx, which may primarily be assured by providing a central concavity at the distal extremity of the instrument head, whereby the larynx is also partly laterally enflanked. Furthermore, the instrument head may be provided on its rear side with an axially extending concavity whereby the said head may fit closely against the pharynx projecting forward a little in this case. This has the consequence that the instrument head cannot move past the larynx upon inserting the instrument along the median line nor deflect the same laterally on the other hand, so that a maximum assurance is provided for the instrument being placed in the correct position as soon as a commensurately great resistance is encountered finally during the inserting operation.

The said passage is formed by the forwardly open channel ending before the instrument head, of a shaft which is substantially semi-circular in cross-section and flexible but otherwise morphologically stable, the channel being intended to merge into slide surfaces at its longitudinaly sides. Furthermore, the channel should be provided with a ramp at the distal extremity or merge into a ramp having a ramp surface rising from the channel base. If the instrument is inserted correctly, the tube initially placed within the channel may be fed foward farther in the distal direction and be pushed reliably and without risk as far as into the windpipe via the ramp directed at the laryngeal cavity of the patient.

Other features of the invention will be described in the following with reference to some specific embodiments which are illustrated in diagrammatical and simplified form in the accompanying drawings.

BRIEF DESCRIPTION OF THE DRAWINGS

FIG. 1 shows a sideview of an instrument in accordance with the invention;

FIG. 2 shows a plan view of the instrument according to FIG. 1,

FIGS. 3 to 6 show different cross-sections corresponding to the sectioning lines III—III, IV—IV, V—V and VI—VI in FIG. 2, FIG. 7 shows the instrument inserted via the oral and laryngeal cavities according to FIGS. 1 to 6.

FIG. 8 shows a plan view of the front side of another form of embodiment of the instrument, FIG. 9 shows a rear view of the instrument illustrated in FIG. 8, FIG. 10 shows a cross-section through the instrument along the sectioning line X—X FIG. 9, FIGS. 11 to 13 show the application of the instrument according to FIGS. 8 to 10 in three different stages.

DETAILED DESCRIPTION OF THE PREFERRED EMBODIMENTS

Figure 12:
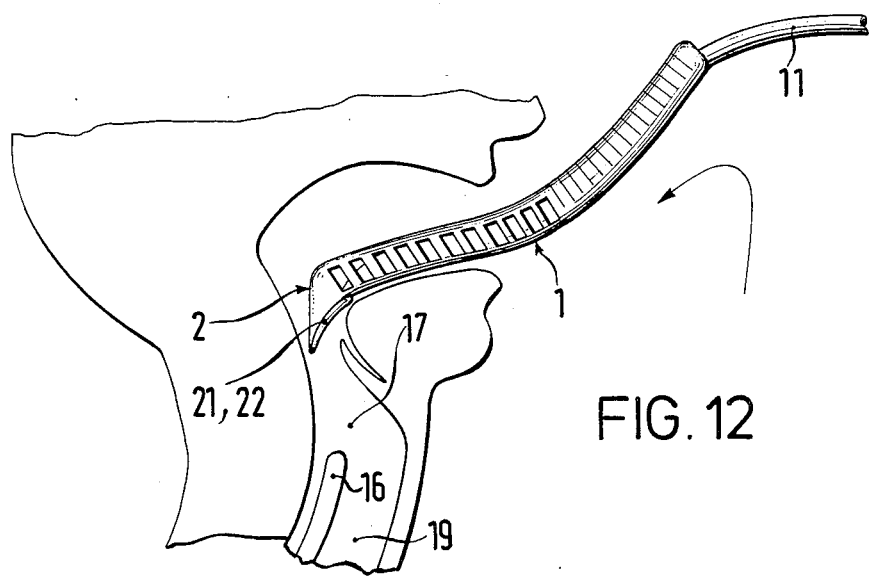

The instrument essentially comprises the shaft 1 and the distal head 2. The shaft, which remains morphologically stable in cross-section even during longitudinal bending, has a longitudinally extending, forwardly open channel 3 terminating before the head 2, which in all the examples illustrated is approximately semicircular in cross-section and at both of its longitudinal sides merges into slide surfaces 4, 5 and distally merges into a ramp 6 comprising a ramp surface rising from the channel base 3a.

In the instrument according to FIGS. 1 to 7, the head 2 has substantially the shape of a bowl, a fork or a spoon, the concave surface 2a of the head being forwardly directed during application of the instrument and is intended to be placed in contact against the larynx whilst inserting the instrument as will be described in detail in the following. In this context, the term "front" means that the parts of the instrument described in this manner are turned towards the physician standing before the patient, whereas the "rear" parts are facing away from the physician. Stated in other terms, this indicates for example that the instrument is seen from the front in FIGS. 2 and 8, wherein the instrument is observed from the rear in FIG. 9.

In the form of embodiment according to FIGS. 1 to 7, the head 2 had a centrally formed concavity 7 at the free extremity, so that the head forms two flaps in the said area, which taper down towards the marginal area. Furthermore, the head has an axially extending concavity 8 on the rear side. Furthermore, the head 2 and the ramp 6 are separated by a web 9 extending transversely between them, whereof the surface may in accordance with the illustration be situated in the same plane as the slide surfaces 4, 5 or also displaced towards the rear for this purpose or displaced towards the left according to FIG. 1.

The instrument may well have a straight extension, but is is also possible for the instrument or its shaft 1 to be produced in curved form to correspond to the anatomical conditions of the oral and pharyngeal cavities, that is to say to make a preliminary selection of approximately the curvature shown in FIG. 7 or a somewhat smaller curvature, whereby the insertion of the instrument could understandably be facilitated. Furthermore, the shaft 1 may be slit open at the rear side in the area of the apex of curvature. Slots 10 of this kind, illustated in FIG. 2, allow of easier flexing of the shaft to the effect of securing a greater curvature and thus a closer adaptation to the extension of the transition between the oral and pharyngeal cavities.

The insertion of a tube 11 is described in the following. The tube is first placed in the trough 3 of the shaft, in a manner such that its distal extremity is situated as closely as possible before the ramp 6. In this connection, the distal terminal surface 12 of the tube 11 formed by the oblique section should have the oval aperture facing forward (FIG. 7) and be held secured in this position, so that no injuries can be caused by the pointed tube extremity during the subsequent insertion of the tube into the windpipe.

As has already been stated in the foregoing, the patient is appropriately placed in the recumbent position, the vertebral column in the area of the neck being intended to be overstretched a little by appropriate rearward inclination of the head, since the instrument may then be inserted more satisfactorily because of the smaller curvature required. The instrument is pushed manually through the oral cavity 13 and onwards through the pharyngeal cavity 14, until the head 2 and the adjacent curbed portion of the shaft 1 bear against the rear pharynx surface 15. During this action, the slide surfaces 4, 5 assure that the instrument may slide easily and without hindrance over the tongue and the distally adjacent portions in the pharyngeal cavity.

The base of the tongue is thereupon pressed over the front row of teeth, in downward and forward direction, so that the instrument may finally be inserted so far that the head 2 bears against the larynx 16 according to FIG. 7, partially enflanks the same from behind and above with its surface 2a and is moreover clamped between the larynx 16 and the rear pharynx surface 15. A portion of the pharynx surface projecting forward at this point is then situated in the rear concavity 8 of the head 2, so that the head 2 is also secured against a lateral displacement. The concavity 7 also acts to the same effect.

Since it is possible, upon doing so, that the larynx 16 may be deformed a little and that the throat opening may be restricted thereby, the instrument should be pulled back again in proximal direction by a particular amount in appropriate cases, to relieve the larynx.

Furthermore, the physician may moreover grasp the larynx on the patient's throat from the outside with his free hand during this action, to convince himself of the correct positioning of the instrument head 2. In this setting, the ramp 6 has its oblique surface aligned on the laryngeal space 17, so that the tube 11 may then be displaced distally in the trough 3 of the shaft 1 until the distal tube extremity—inclusive of the bulbosity 18 fastened on the tube periphery—has been displaced over the tamp 6 and into the windpipe 19 (FIG. 7). The bulbosity or balloon may then be inflated in a known manner via a hose not shown in particular and leading to the proximal instrument extremity, so that it may fit closely against the windpipe. Following this action, the instrument may be withdrawn again whereas the tube 11 remains secured within the windpipe by means of the inflated balloon.

The reason and purpose of an intubation of this kind are generally known, so that mention is merely made at this point that artificial respiration may be example be administered to the patient via the tube 11 or that secretions may be sampled, or instruments, curative agents or the like, may be inserted into the respiratory tract via the tube 11.

Upon dimensioning the instrument, it is of overall importance that the aperture of the trough 3 should not be wider than the epiglottis 20, since the slide surfaces 4, 5 are intended to be in contact with the epiglottis during the insertion of the instrument. Furthermore, the internal diameter of the trough 3 should be selected so that the tube 11 is wholly accommodated within the trough and does not project outwards over the slide surfaces. This does not exclude the possibility however that a greater diameter may still be imparted to the tube 11, so that the slide surfaces may be omitted in principle, since the function of the slide surfaces may be assumed by the forwardly directed periphery of the tube.

Furthermore, the web 9 should be so narrow that even the shortest epiglottis anatomically encountered is still lifted off upon inserting the instrument. The ramp 6 may moreover only have an inclination such that even tubes 11 of large diameter may assume the necessary secondary curvature at the point of transition from the laryngeal cavity 17 into the windpipe 19 and cannot have the distal extremity seized within the laryngeal cavity. Finally, the head 2 may be more easily bendable than the shaft 1 in an instrument of this kind, since the insertion of the instrument could otherwise be rendered difficult and the risk of injuries could otherwise prevail.

FIGS. 8 to 13 show another example of embodiment for an instrument in accordance with the invention. To the extent that parts of this instrument correspond in nature and function to those of the previously described example, identical reference symbols were used for such parts.

The instrument head 2 comprises two flexible flaps 21, 22 which are situated on the outer rim of a fork-shaped element 23 and overlap each other. Upon inserting the instrument, these flaps come into contact with the larynx 16 (FIG. 13) and are rearwardly deflected upon doing so, so that they will partially enflank the larynx.

The proximal extremities 21a, 22a of the flaps lie in the extension of the surface of the ramp 6 which rises slopingly in distal direction from the ramp base 3a, so that they are flexibly bent a little in forward direction by the extremity of the tube 11 which is to be pushed over the ramp, the tip of the tube first and thereupon the tube itself being guided centred between the slightly spread apart flap extremities and being prevented from being deflected sideways.

Figure 13:
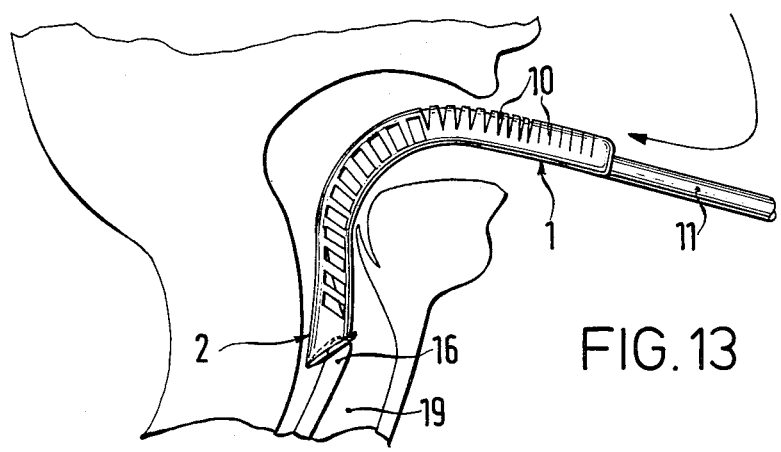

FIGS. 11 to 13 show the insertion of the instrument in three principal stages. So that the bending of the head 2 may be facilitated and remotely controlled in some degree during the insertion stage according to FIG. 12, the shaft 1 is equipped at both longitudinal sides with rails 24, 25 which simultaneously assure the function of the aforesaid slide surfaces 4, 5. Another rail 26 is moreover installed on the shaft 1 and opposite to the channel base 3a. These three rails may be joined to the fully prepared shaft by interwelding or bonding. The possibility is evidently also available on the other hand that the rails may already be embedded as well in the shaft material during the production of the shaft.

The three rails extend either up to or into the region of the head 2 and are more rigid than the comparatively soft material of the shaft. Once the physician has inserted the instrument as far as shown in FIG. 11, he may use one hand to bend the head 2 according to FIG. 12, for example by exercising a distally directed thrust with the surface of the hand on the rail 26, and a proximally directed traction on the rails 24, 25 by means of the thumb or fingers.

The instrument may thereupon be pushed in further easily and without risk of injury into the position according to FIG. 13, the traction and thrust situations on the rails being due to be reversed before this position is reached, so that the head 2 may safely pass beside the larynx 16 to arrive behind the latter.

The forces necessarily engendered for deforming the shaft material are reduced if the part of the shaft 1 forming the trough is equipped with window-like perforations 27 in the area of the rail 26, which are situated in the two sidewalls of the shaft adjacent to the trough base 3a. Furthermore, the mobility of the head 2 with respect to the shaft 1 may be improved in a manner such that the head is flexibly joined to the shaft. For example, this may be accomplished if the cross-section of the instrument at the point of transition from the shaft to the head is constricted or made smaller than the cross-sections adjacent thereto.

The shaft 1 also has slots 10 moreover, in this example of embodiment, that is to say in the area of the one curvature required during insertion of the instrument (FIG. 13), the slots severing the shaft material in the area of the channel base 3a and also extending into the two adjacent sidewalls of the channel or of the shaft.

As already stated in connection with the example of embodiment according to FIGS. 1 to 7, the physician may—as soon as the instrument has been placed in the position shown in FIG. 13 and an additional correction of the position reached has been performed if appropriate by further insertion or extraction of the instrument—push the tube 11 over the ramp 6 into the space 17 and onwards into the windpipe 19, so that the situation also also shown in FIG. 7 for example is the result, and the instrument may subsequently be pulled out again completely, whereas the tube 11 is left in its position.

If it is not intended to utilize the instrument to perform intubations but merely to keep clear the upper respiratory passages, the instrument is placed in the position illustrated in FIGS. 7 and 13 without a tube, so that respiratory passages are kept clear mandatorily and the patient is able to breathe through unobstructed passages which are established by the instrument passage on the one hand, and on the other hand also by spaces formed beside the inserted instrument.

Figures 14, 15:
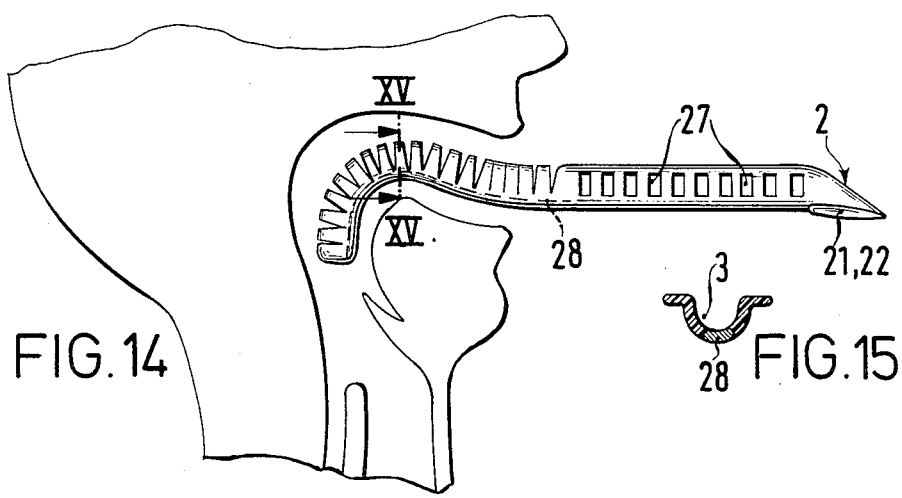
FIG. 14 shows the instrument illustrated in FIGS. 9 to 13, but with a different form in the proximal region.
FIG. 15 shows a cross-section through the instrument according to FIG. 14 along the sectioning line XV—XV.

To this effect, FIGS. 14 and 15 finally also show a comparatively uncomplicated solution in which the proximal extremity of the instrument may also be utilised to keep clear the upper respiratory passages in the manner of a "Guedel" tube known per se, if an internal or external adjunct 28 stabilising the shaft in the form established by bending in each case (FIG. 14), or more than one, is present in or on the shaft 1. This insert embedded in the shaft material or attachment fastened on the shaft, may consist of a rail, for example of mild steel, copper and the like, and as illustrated may extend over the area of the shaft which is also equipped with the slots 10.

Before the instrument constructed in this manner is inserted with its proximal extremity leading, the physician may bend this extremity in accordance with the anatomical characteristics of the patient, possibly under application of a template, and insert the same through the mouth and into a pharyngeal cavity, for example to look after a patient provisionally in cases of acute need and to be able to ensure that the respiratory passages are kept clear and are not blocked by a possible rearwardly directed drop of the tongue.

The tubes 11 available in the trade commonly have a distal extremity which is formed by means of a cut taken obliquely with respect to the axis of the tube. Such comparatively pointed tube extremities may easily lead to injuries upon being inserted. For this reason, it seems to be appropriate to equip the distal tube extremity with a slider element which may be pulled into the tube extremity from the outside by means of a wire or other connecting element which is to be inserted into the tube from the distal end, so that with an appropriate shape of the slider element, it is possible to fill the asymmetrical space beside the obliquely chamfered tube extremity.

A slider element of this nature may for example have the form of a closed loop which is pulled into the area of the tube extremity by means of a wire led through the tube, and locks itself against farther displacement within the tube by forces acting from the outside, but acquires a smaller diameter upon pulling on the wire and may easily be pulled out again through the tube.

Tests have shown that it is possible to operate satisfactorily in practice with both the instruments described and illustrated. The form of embodiment according to FIGS. 8 to 10 could however have particular and greater advantages during the insertion of the instrument. Although the flaps 21 22 should consist of comparatively soft material, they should still slide without being deformed over the epiglottis projecting into the insertion passage available and be adapted to push the same away forwards out of the passage. The epiglottis should consequently be prevented from being downwardly entrained by the distally displaced instrument head.

Furthermore, the two flaps 21 22 will be moved rearwards obliquely upon bearing against the larynx 16 (FIG. 13) and will thereby enflank the larynx laterally as well as from above and behind, the maximum rearward deflection of the flexible flaps being intended to be limited by a stop, in a manner which that the instrument head 2 cannot slip downwards too far behind the larynx 16. A stop of this nature is formed by the fork-shaped part 23 of the instrument head in the example illustrated.

The rails 24, 25 and 26 need not mandatorily be separate components which are installed on the shaft 1 or embedded in its material. "Rails" having the same action also result if the material of the shaft in the two longitudinal sides and in the channel base is more rigid under longitudinally directed thrust or traction than the remainder of the material in the shaft sidewalls, which may commonly already be assured by the incorporation of the perforations 27 in the sidewalls.

In conclusion, it is also pointed out that a shaft 1 comprising an open channel 3 will facilitate the insertion of the tube 11 on the one hand and on the other hand also the withdrawal of the instrument after the tube has been fed forward into the windpipe 19. It is also possible however to construct the shaft as a pipe which is closed say as far as the ramp 6, in which case it seems to be appropriate however to slit the pipe open longitudinally at the front in this case, so that the pipe may spread open in the area of the longitudinal slot upon withdrawing the instrument to allow the tube to emerge.

What is claimed is:

1. In an instrument for keeping clear the upper respiratory passages and for performing intubations, comprising a shaft with a passage to enable a tube to be inserted with its distal extremity moving as far as into the trachea with said passage acting as a guide, an improvement characterized in that the passage is constructed as a channel extending within the shaft of the instrument and the distal extremity of the instrument comprises a head before which terminates the said channel and which at the time of inserting the instrument is to be placed in contact wit the larynx and acts as a stop to limit the maximum distance of insertion, including a ramp formed at the distal extremity of the channel, the surface of said ramp rising from the bottom of the channel, and wherein said head comprises two mutually overlapping flaps which are flexibly displaceable rearwards upon coming into contact with the larynx, and wherein the proximal extremities of the flaps lie in the extension of the ramp surface and form a centering guide for a tube to be pushed over the ramp in the distal direction.

* * * * *